United States Patent [19]

Young et al.

[11] Patent Number: 5,376,638
[45] Date of Patent: Dec. 27, 1994

[54] METHODS FOR TREATING RENIN-RELATED DISORDERS WITH AMYLIN ANTAGONISTS

[75] Inventors: Andrew A. Young, San Diego; Timothy J. Rink, La Jolla, both of Calif.

[73] Assignee: Amylin Pharmaceuticals, Inc., San Diego, Calif.

[21] Appl. No.: 939,106

[22] Filed: Sep. 1, 1992

[51] Int. Cl.$^5$ .................... A61K 37/02; C07K 7/10
[52] U.S. Cl. ........................................ 514/12; 514/11; 514/13
[58] Field of Search ..................... 514/11-13

[56] References Cited

U.S. PATENT DOCUMENTS 5,112,945  5/1992  Westermark et al. ............... 530/324
5,124,314  6/1992  Cooper ..................................... 514/4

*Primary Examiner*—Lester L. Lee
*Attorney, Agent, or Firm*—Lyon & Lyon

[57] ABSTRACT

Methods for treating conditions associated with elevated, inappropriate or undesired renin activity are disclosed which comprise administration of an effective amount of any amylin antagonist alone or in conjunction with other anti-hypertensive agents. Methods for screening for and/or evaluating anti-renin amylin antagonists are also described.

9 Claims, 7 Drawing Sheets

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
( A ) LENGTH: 30 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

VTHRLAGLLS RSGGVVKNNF VPTNVGSKAF 30

( 2 ) INFORMATION FOR SEQ ID NO:2:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

ATQRLANFLV HSSNNFGAIL SSTNVGSNTY        30

( 2 ) INFORMATION FOR SEQ ID NO:3:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

MLGTYTQDFN KFHTFPQTAI GVGAP        25

( 2 ) INFORMATION FOR SEQ ID NO:4:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

VTHRLAGLLS RSGGVVKNNF VPTNVGSKAF        30

( 2 ) INFORMATION FOR SEQ ID NO:5:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

ATQRLANFLV RSSNNLGPVL PPTNVGSNTY        30

( 2 ) INFORMATION FOR SEQ ID NO:6:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

VLGKLSQELH KLQTYPRTNT GSGTP        25

( 2 ) INFORMATION FOR SEQ ID NO:7:

( i ) SEQUENCE CHARACTERISTICS:
        ( A ) LENGTH: 25 amino acids
        ( B ) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:7:

VLGKLSQELH KLQTYPRTDV GAGTP    25

( 2 ) INFORMATION FOR SEQ ID NO:8:

( i ) SEQUENCE CHARACTERISTICS:
( A ) LENGTH: 25 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:8:

VLGKLSQELH KLQTYPRTNT GSDTY    25

( 2 ) INFORMATION FOR SEQ ID NO:9:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:9:

LGRLSQELHR LQTYPRTNTG SNTY    24

( 2 ) INFORMATION FOR SEQ ID NO:10:

( i ) SEQUENCE CHARACTERISTICS:
( A ) LENGTH: 30 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:10:

VTHRLADFLS RSGGVGKNNF VPTNVGSKAF    30

( 2 ) INFORMATION FOR SEQ ID NO:11:

( i ) SEQUENCE CHARACTERISTICS:
( A ) LENGTH: 29 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:11:

THRLAGLLSR SGGVVKNNFV PTNVGSKAF    29

( 2 ) INFORMATION FOR SEQ ID NO:12:

( i ) SEQUENCE CHARACTERISTICS:
( A ) LENGTH: 27 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:12:

RLAGLLSRSG GVVKNNFVPT NVGSKAF                27

(2) INFORMATION FOR SEQ ID NO:13:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

RSGGVVKNNF VPTNVGSKAF                         20

(2) INFORMATION FOR SEQ ID NO:14:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

VLGKLSQELH KLQTYPRTDV GAGTP                   25

(2) INFORMATION FOR SEQ ID NO:15:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

VLGKLSQELH KLQTYPRTNT GSNTY                   25

(2) INFORMATION FOR SEQ ID NO:16:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

LGKLSQELHK LQTYPRTNTG SGTP                    24

(2) INFORMATION FOR SEQ ID NO:17:

(i) SEQUENCE CHARACTERISTICS:
        (A) LENGTH: 24 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

LGKLSQELHK LQTYPRTNTG SNTY                    24

(2) INFORMATION FOR SEQ ID NO:18:

(i) SEQUENCE CHARACTERISTICS:
        (A) LENGTH: 24 amino acids ( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:18:

LGKLSQELHK LQTYPSTNVG SNTY                     24

( 2 ) INFORMATION FOR SEQ ID NO:19:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:19:

LGKLSQELHK LQTYPSTNVG SNTY                     24

( 2 ) INFORMATION FOR SEQ ID NO:20:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:20:

LGKLSQELHK LQTYPSTNVG SNTY                     24

( 2 ) INFORMATION FOR SEQ ID NO:21:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:21:

LGRLSQLLHK RQTYPRTNTG SNTY                     24

( 2 ) INFORMATION FOR SEQ ID NO:22:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:22:

LGRLSQELHR LQTYPRTNTG SNTY                     24

( 2 ) INFORMATION FOR SEQ ID NO:23:

( i ) SEQUENCE CHARACTERISTICS:
( A ) LENGTH: 24 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:23:

LGRLSQELHR LQTYPRTNTG SNTY    24

( 2 ) INFORMATION FOR SEQ ID NO:24:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:24:

LGKLSQE LHRLQTYPRT NTGSNTY    25

( 2 ) INFORMATION FOR SEQ ID NO:25:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:25:

VLGKLSQE LHKLQTYPRT NTGSNTY    25

( 2 ) INFORMATION FOR SEQ ID NO:26:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:26:

VLGKLSQELH KLQTYPRTNT GSNTY    25

( 2 ) INFORMATION FOR SEQ ID NO:27:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:27:

VLGKLSQELH KLQTYPRTNT GSNTY    25

( 2 ) INFORMATION FOR SEQ ID NO:28:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:28:

VLGKLSQELH KLQTYPRTNT GSNTY    25

METHODS FOR TREATING RENIN-RELATED DISORDERS WITH AMYLIN ANTAGONISTS

FIELD OF THE INVENTION

The present invention relates to methods for inhibiting amylin-stimulated release of renin. More particularly, the invention relates to the use of antagonists of amylin in the treatment of renin-related disorders. The invention also relates to methods of identifying amylin antagonists for use in said treatments.

BACKGROUND

Amylin

Amylin is a 37 amino acid protein hormone. It was isolated, purified and chemically characterized as the major component of amyloid deposits in the islets of pancreases of human Type 2 diabetics (Cooper et al., Proc. Natl. Acad. Sci., USA, 84:8628-8632 (1987)). The amylin molecule has two important post-translational modifications: the C-terminus is amidated, and the cysteines in positions 2 and 7 are cross-linked to form an N-terminal loop. The sequence of the open reading frame of the human amylin gene shows the presence of the Lys-Arg dibasic amino acid proteolytic cleavage signal, prior to the N-terminal codon for Lys, and the Gly prior to the Lys-Arg proteolytic signal at the C-terminal position, a typical sequence for amidation by protein amidating enzyme, PAM (Cooper et al., Biochem. Biophys. Acta, 1014:247-258 (1989)). Amylin is the subject of United Kingdom patent application Serial No. 8709871, filed Apr. 27, 1987, and corresponding U.S. applications filed Apr. 27, 1988, Nov. 23, 1988 and May 2, 1989.

In Type 1 diabetes, amylin has been shown to be deficient and combined replacement with amylin has been proposed as a preferred treatment over insulin alone, for instance in limiting hypoglycemic episodes. The use of amylin for the treatment of diabetes mellitus is the subject of United Kingdom patent application Serial No. 8720115 filed on Aug. 26, 1987, by G. J. S. Cooper, and filed as patent application Ser. No. 236,985 in the United States on Aug. 26, 1988. Pharmaceutical compositions containing amylin and amylin plus insulin are described in U.S. Pat. No. 5,124,314, issued Jun. 23, 1992.

Excess amylin action mimics key features of Type 2 diabetes and amylin blockade has been proposed as a novel therapeutic strategy. It has been disclosed in commonly-owned copending U.S. patent application Ser. No. 275,475, filed Nov. 23, 1988 by Cooper, G. J. S. et al., the contents of which are incorporated herein by reference, that amylin causes reduction in both basal and insulin-stimulated incorporation of labelled glucose into glycogen in skeletal muscle. The latter effect was also disclosed to be shared by CGRP (see also Leighton, B. and Cooper, G. J. S., Nature, 335:632-635 (1988)). Amylin and CGRP were approximately equipotent, showing marked activity at 1 to 10 nM. Amylin is also reported to reduce insulin-stimulated uptake of glucose into skeletal muscle and reduce glycogen content (Young et al., Amer. J. Physiol. 259:457-461 (1990)). The treatment of Type 2 diabetes and insulin resistance with amylin antagonists is disclosed.

Both the chemical structure and the gene sequence amylin have been said to support the determination that it is a biologically active or "messenger" molecule. The chemical structure is nearly 50% identical to the calcitonin-gene-related peptides (CGRP), also 37 amino acid proteins which are widespread neurotransmitters with many potent biological actions, including vasodilation. Amylin and CGRP share the $^2$Cys-$^7$Cys disulfide bridge and the C-terminal amide, both of which are essential for full biologic activity (Cooper et al. Proc. Natl. Acad. Sci., 85-7763-7766 (1988)).

Amylin may be one member of a family of related peptides which include CGRP, insulin, insulin-like growth factors, and the relaxins and which share common genetic heritage (Cooper, G. J. S., et al., Prog. Growth Factor Research 1:99-105 (1989)). The two peptides calcitonin and CGRP-1 share common parentage in the calcitonin gene where alternative processing of the primary mRNA transcript leads to the generation of the two distinct peptides, which share only limited sequence homology (about 30%) (Amara, S. G. et al., Science, 229:1094-1097 (1985)). The amylin gene sequence is typical for a secreted messenger protein, with the mRNA coding a prepropeptide with processing sites for production of the secreted protein within the Golgi or secretory granules. Amylin is mainly co-localized with insulin in beta cell granules and may share the proteolytic processing enzymes that generate insulin from pro-insulin.

Amylin is primarily synthesized in pancreatic beta cells and is secreted in response to nutrient stimuli such as glucose and arginine. Studies with cloned beta-cell tumor lines (Moore et al., Biochem. Biophys. Res. Commun., 179(1) (1991)), isolated islets (Kanatsuka et al., FEBS Lett., 259(1), 199-201 (1989)) and perfused rat pancreases (Ogawa et al., J. Clin. Invest., 85:973-976 (1990)) have shown that short pulses, 10 to 20 minutes, of nutrient secretagogues such as glucose and arginine, stimulate release of amylin as well as insulin. The molar amylin:insulin ratio of the secreted proteins varies between preparations from about 0.01 to 0.4, but appears not to vary much with different stimuli in any one preparation. However, during prolonged stimulation by elevated glucose, the amylin:insulin ratio can progressively increase (Gedulin et al., Biochem. Biophys. Res. Commun., 180(1):782-789 (1991)). Thus, perhaps because gene expression and rate of translation are independently controlled, amylin and insulin are not always secreted in a constant ratio.

Amylin-like immunoreactivity has been measured in circulating blood in rodents and humans by a variety of radioimmunoassays all of which use rabbit anti-amylin antiserum, and most of which use an extraction and concentration procedure to increase assay sensitivity. In normal humans, fasting amylin levels from 1 to 10 pM and post-prandial or post-glucose levels of 5 to 20 pM have been reported (e.g., Hartter et al., Diabetologia, 34:52-54 (1991)); Sanke et al., Diabetologia, 34:129-132 (1991)); Koda et al., The Lancet, 339:1179-1180 (1992)). In obese, insulin-resistant individuals, post-food amylin levels can go higher, reaching up to about 50 pM. For comparison, the values for fasting and post-prandial insulin are 20 to 50 pM, and 100 to 300 pM respectively in healthy people, with perhaps 3- to 4-fold higher levels in insulin-resistant people. In Type 1 diabetes, where beta-cells are destroyed, amylin levels are at or below the levels of detection and do not rise in response to glucose (Koda et al., The Lancet, 339, 1179-1180 (1992)). In normal mice and rats, basal amylin levels have been reported from 30 to 100 pM, while values up to 600 pM have been measured in certain insulin-resistant, diabetic strains of rodents (e.g., Huang et al., *Hypertension,* 19:I-101–I-109 (1991)); Gill et al., *Life Sciences,* 48:703–710 (1991)).

It has been discovered that certain actions of amylin are similar to known non-metabolic actions of CGRP and calcitonin; however, the metabolic actions of amylin discovered during investigations of this newly identified protein appear to reflect its primary biologic role. At least some of these metabolic actions are mimicked by CGRP, albeit at doses which are markedly vasodilatory (see, e.g., Leighton et al., *Nature,* 335:632–635 (1988)); Molina et al., *Diabetes,* 39:260–265 (1990)).

The first discovered action of amylin was the reduction of insulin-stimulated incorporation of glucose into glycogen in rat skeletal muscle (Leighton et al., *Nature,* 335:632–635 (1988)); the muscle was made "insulin-resistant". Subsequent work with rat soleus muscle ex-vivo and in vitro has indicated that amylin reduces glycogen synthase activity, promotes conversion of glycogen phosphorylase from the inactive b form to the active a form, promotes net loss of glycogen (in the presence or absence of insulin), increases glucose-6-phosphate levels, and can increase lactate output (see, e.g., Deems et al., *Biochem. Biophys. Res. Commun.,* 181(1):116–120 (1991)); Young et al., *FEBS Letts,* 281(1,2):149–151 (1991)). Whether amylin interferes with glucose transport per se is uncertain (see e.g. Young et al., *Am. J. Physiol.,* 259:E457–E461 (1990); Zierath et al., *Diabetologia,* 35:26–31 (1992)). Studies of amylin and insulin dose-response relations show that amylin acts as a non-competitive or functional antagonist of insulin in skeletal muscle (Young et al., *Am. J. Physiol., Am. J. Physiol.,* 263(2):E274–E281 (1992)). Thus, at an effective concentration of amyrin, no concentration of insulin can overcome amylin action. There is no evidence that amylin interferes with insulin binding to its receptors, or the subsequent activation of insulin receptor tyrosine kinase (Follett et al., *Clinical Research* 39(1):39A (1991)); Koopmans et al., *Diabetologia,* 34, 218–224 (1991)). The actions of amylin on skeletal muscle resemble those of adrenaline (epinephrine). However, while adrenaline's actions are believed to be mediated largely by cAMP, some workers have concluded that amylin's actions are not mediated by cAMP (see Deems et al., *Biochem. Biophys. Res. Commun.,* 181(1):116–120 (1991)).

It is believed that amylin acts through receptors present in plasma membranes. It has been reported that amylin works in skeletal muscle via a receptor-mediated mechanism that promotes glycogenolysis, by activating the rate-limiting enzyme for glycogen breakdown, phosphorylase a (Young, A. et al., *FEBS Letts,* 281:149–151 (1991)). Studies of amylin and CGRP, and the effect of the antagonist [8-37]CGRP, suggest that amylin acts via its own receptor (Wang et al., *FEBS Letts.,* 219:195–198 (1991 b)), counter to the conclusion of other workers that amylin may act primarily at CGRP receptors (e.g., Chantry et al., *Biochem. J.,* 277:139–143 (1991)); Galeazza et al., *Peptides,* 12:585–591 (1991)); Zhu et al., *Biochem. Biophys. Res. Commun.,* 177(2):771–776 (1991)).

While amylin has marked effects on hepatic fuel metabolism in vivo, there is no general agreement as to what amylin actions are seen in isolated hepatocytes or perfused liver. The available data do not support the idea that amylin promotes hepatic glycogenolysis, i.e., it does not act like glucagon (e.g., Stephens, et al., *Diabetes,* 40:395–400 (1991)); Gomez-Foix et al., *Biochem J.,* 276:607–610 (1991)). It has been suggested that amylin may act on the liver to promote conversion of lactate to glycogen and to enhance the amount of glucose able to be liberated by glucagon (see Roden et al., *Diabetologia,* 35:116–120 (1992)). Thus, amylin could act as an anabolic partner to insulin in liver, in contrast to its catabolic action in muscle.

The effect of amylin on regional hemodynamic actions, including renal blood flow, in conscious rats was recently reported (Gardiner et al., *Diabetes,* 40:948–951 (1991)). The authors noted that infusion of rat amylin was associated with greater renal vasodilation and less mesenteric vasoconstriction than is seen with infusion of human α-CGRP. They concluded that, by promoting renal hyperemia to a greater extent than did α-CGRP, rat amylin could cause less marked stimulation of the renin-angiotensin system, and thus, less secondary angiotensin II-mediated vasoconstriction. It was also noted, however, that during coninfusion of human α-[8-37]CGRP and rat amylin renal and mesenteric vasoconstrictions were unmasked, presumably due to unopposed vasoconstrictor effects of angiotensin II, and that this finding is similar to that seen during coninfusion of human α-CGRP and human α-[8-37]CGRP (id. at 951).

In fat cells, contrary to its adrenalin-like action in muscle, amylin has no detectable actions on insulin-stimulated glucose uptake, incorporation of glucose into triglyceride $CO_2$ production (Cooper et al., *Proc. Natl. Acad. Sci.,* 85:7763–7766 (1988)) epinephrine-stimulated lipolysis, or insulin-inhibition of lipolysis (Lupien and Young, "Diabetes Nutrition and Metabolism—Clinical and Experimental" (in press). Amylin thus exerts tissue-specific effects, with direct action on skeletal muscle, marked indirect (via supply of substrate) and perhaps direct effects on liver, while adipocytes appear "blind" to the presence or absence of amylin. No direct effects of amylin on kidney tissue have been reported.

It has also been reported that amylin can have marked effects on secretion of insulin. In isolated islets (Ohsawa et al., *Biochem. Biophys. Res. Commun.,* 160(2):961–967 (1989)), in the perfused pancreas (Silvestre et al., *Reg. Pept.,* 31-23-31 (1991)), and in the intact rat (Young et al., *Mol. Cell. Endocrinol.,* 84:R1–R5 (1992)), some experiments indicate that amylin down-regulates insulin secretion. The perfused pancreas experiments point to selective down-regulation of the secretory response to glucose with sparing of the response to arginine. Other workers, however, have been unable to detect effects of amylin on isolated β-cells, on isolated islets, or in the whole animal (see Broderick et al., *Biochem. Biophys. Res. Comm.,* Vol. 177:932–938 (1991) and references therein).

The most striking effect of amylin in vivo is stimulation of a sharp rise in plasma lactate, followed by a rise in plasma glucose (Young et al., *FEBS Letts,* 281(1,2):149–151 (1991)). Evidence indicates that the increased lactate provides substrate for glucose production and that amylin actions can occur independent of changes in insulin or glucagon. In "glucose clamp" experiments, amylin infusions cause "insulin resistance", both by reducing peripheral glucose disposal, and by limiting insulin-mediated suppression of hepatic glucose output (e.g., Frontoni et al., *Diabetes,* 40:568–573 (1991)); Koopmans et al., *Diabetologia,* 34, 218–224 (1991)).

In lightly anesthetized rats which were fasted for 18 hours to deplete their stores of hepatic glycogen, amylin injections stimulated rises in plasma lactate from about 0.5 to 1.5 mM followed by a prolonged increase in plasma glucose levels from about 6 to 11 mM. These effects were observed for both intravenous and subcutaneous injections (Young et al., *FEBS Letts,* 281(1,2):149–151 (1991)). The effects of amylin in fed animals differ quantitatively from its effects in fasted animals. In fed rats, with presumably normal liver glycogen stores, amylin causes a more pronounced and prolonged rise in plasma lactate; however, there is only a modest rise in plasma glucose. It has been suggested that amylin promotes the "return limb" of the Cori cycle, i.e., muscle glycogen via breakdown to lactate provides substrate for hepatic gluconeogenesis and glycogen production and probably triglyceride synthesis. Insulin drives the forward limb, i.e., uptake of glucose into muscle and production of muscle glycogen. Insulin and amylin can thus be seen as partners in regulating the "indirect" pathway of post-prandial hepatic glycogen repletion. "Insulin resistance" in muscle and liver may be under normal, physiologic regulation by amylin.

Non-metabolic actions of amylin include vasodilator effects which may be mediated by interaction with CGRP vascular receptors. Reported in vivo tests suggest that amylin is at least about 100 to 1000 times less potent than CGRP as a vasodilator (Brain et al., *Eur. J. Pharmacol.,* 183:2221 (1990); Wang et al., *FEBS Letts.,* 291:195–198 (1991)). Injected into the brain, amylin has been reported to suppress food intake (e.g., Chance et al., *Brain RES.,* 539, 352–354 (1991)), an action shared with CGRP and calcitonin. The effective concentrations at the cells that mediate this action are not known. Amylin has also been reported to have effects both on isolated osteoclasts where it caused cell quiescence, and in vivo where it was reported to lower plasma calcium by up to 20% in rats, in rabbits, and in humans with Paget's disease ( see, e.g., Zaidi et al., *J. Bone Mineral Res.,* S293 (1990). From the available data, amylin seems to be 10 to 30 times less potent than human calcitonin for these actions. Interestingly, it was reported that amylin appeared to increase osteoclast cAMP production but not to increase cytosolic $Ca^{2+}$, while calcitonin does both (Alam et al., *Biochem. Biophys. Res. Commun.,* 179(1):134–139 (1991)). It was suggested, though not established, that calcitonin may act via two receptor types and that amylin may interact with one of these.

Infusing amylin receptor antagonists may be used to alter glucoregulation. $^{8-37}$CGRP is a demonstrated amylin blocker in vitro and in vivo (Wang et al., *Biochem. Biophys. Res. Commun.,* 181(3):1288–1293 (1991)), and was found to alter glucoregulation following an arginine infusion in fed rats (Young et al., *Mol. Cell. Endocrino.,* 84:R1–R5 (1992)). The initial increase in glucose concentration is attributed to arginine-stimulated glucagon secretion from islet alpha cells; the subsequent restoration of basal glucose is attributed to insulin action along with changes in other glucoregulatory hormones. When the action of amylin is blocked by preinfusion of $^{8-37}$hCGRP, the initial glucose increase is not significantly different, but there is a subsequent fall in glucose concentration to well below the basal level, which is restored only after some 80 minutes. Thus, glucoregulation following this challenge with an islet secretagogue was altered by infusion of an amylin receptor antagonist. Additionally, insulin concentrations were measured at half hour intervals and it was found that insulin concentration 30 minutes following the arginine infusion was almost twice as high in animals infused with an amylin receptor antagonist as in the normal controls. $^{8-37}$CGRP is also an effective CGRP antagonist. However, very similar results were seen with another amylin antagonist, AC66, which is selective for amylin receptors compared with CGRP receptors (Young et al., *Mol. Cell. Endocrino.,* 84:R1–R5 (1992)). These results are said to support the conclusion that blockade of amylin action can exert important therapeutic benefits in Type 2 diabetes.

Patients with Type 1 diabetes, in addition to a lack of insulin, are reported to have marked amylin deficiency. As noted above, data show that amylin expression and secretion by pancreatic beta-cells is absent or well below normal in Type 1 diabetes. In several animal models of Type 1 diabetes, amylin secretion and gene expression are depressed (Cooper et al., *Diabetes,* 497–500 (1991); Ogawa et al., *J. Clin. Invest.,* 85:973–976 (1990)). Measurements of plasma amylin in Type I diabetic patients show that amylin is deficient in these patients after an overnight fast, and that a glucose load does not elicit any increase in amylin levels (Koda et al., *The Lancet,* 339:1179–1180 (1992)).

Renin

The renin-angiotensin system is an extensively studied physiological control system; among its key functions are the regulation of body fluid and ionic composition, renal function and blood pressure. Excessive or inappropriate activity is well recognized as an important cause of hypertension and a contributor to the problems of heart failure. Methods of inhibition of the renin-angiotensin system have been developed as important treatments for hypertension and heart failure. A summary of the physiology, pharmacology, pathology and clinical aspects of this area is set out in Chapter 27 (page 639–653) of Goodman & Gilman's "The Pharmacological Basis of Therapeutics" (7th Edition, 1985).

Renin is a highly specific aspartyl proteinase of molecular weight about 40,000 Daltons, produced and secreted by juxtaglomerula cells of the kidney. Renin acts on the plasma substrate, angiotensinogen, to split off the non-inactive decapeptide angiotensin I. Angiotensin I is in turn converted to angiotensin II, the major bioactive molecule in this "cascade". Renin in itself has no recognized biological activity beyond its action as a proteolytic enzyme; rather it can be considered to be an endocrine factor, derived from renal tissue. Renal renin release is reported to be stimulated by several mechanisms, including: falls in blood pressure; reduced blood volume; reduced plasma sodium concentration; $\beta$-adrenoceptor stimulation by circulating epinephrine or sympathetic nerve activity; and a variety of other bioactive molecules, such as prostaglandins, cytokines, and growth factors whose physiologic and pathologic relevance is less or not at all clear. There is renin production in certain other locations, particularly the brain where the renin-angiotensin system is thought to be a local regulator. The very low levels of plasma renin activity observed after removal of the kidneys indicates that most of circulating renin is of renal origin.

The main biological and medical importance of renin is believed to reside in its ability to generate angiotensins from angiotensinogen. It is currently considered that most of the biologic and pathologic actions of renin are due to the bioactivity of angiotensin II. Other enzymes, widely distributed in the body, are capable of further degrading angiotensin II to angiotensin III and then to inactive peptide fragments. Angiotensin III is not regarded to have important biological activity but rather to be an inactive metabolite of angiotensin II.

The first discovered activity of angiotensin II was a potent ability to increase the blood pressure in intact animals. This effect is now believed to occur by both direct action on blood vessels and indirectly by activation of the sympathetic nervous system. In man, the actions of angiotensin, when directly infused intravenously, are believed to result mainly from a direct action on small blood vessels which in most cases are constricted, thereby increasing the resistance to flow and raising the blood pressure. Angiotensin also acts directly on cardiac muscle cells with a number of consequences including an increase in the force of contraction. The various acute actions of angiotensin on the heart and on the arterial and venous vasculature typically result in a small decrease in cardiac output and because of the constriction, the work of the heart is generally increased.

Angiotensin also has important actions on the adrenal cortex, an endocrine gland an important function of which is the secretion of aldosterone. Angiotensin at very low concentrations directly stimulates the synthesis and secretion of aldosterone. Aldosterone acts on the kidney to enhance the retention of sodium, and retention of sodium, when excessive, is considered an important contributor to hypertension and to the problems of heart failure. Excessive or inappropriate secretion of renin with consequent excess production of angiotensin and consequent excess production of aldosterone can therefore contribute to these pathologic conditions.

Yet another action of angiotensin is on kidney tissue itself where, by action on both intra-renal blood vessels and renal tubules, low concentrations of angiotensin (in the range found in normals subjects and those with hypertension and heart failure) produces an increase of sodium and fluid retention which can contribute to both hypertension and heart failure. It is important to emphasize that concentrations of circulating renin and angiotensin II found in normal individuals, or individuals with essential hypertension fall in the range where there is promotion of aldosterone secretion, action on the kidney, but little or no actual vasoconstriction. Higher levels are required for the vasoconstriction and directly consequent acute blood pressure to occur. But, modestly elevated levels, by the effect on the kidney and body fluid balance, will lead to chronically elevated blood pressure and contribute to the problems of cardiac failure. See, e.g., Chapters 14 and 15 in Hladky & Rink, "Body Fluid and Kidney Physiology" (Edward Arnold, London, 1986).

The concept that excess or inappropriate renin secretion with consequent excess or inappropriate angiotensin formation and action importantly contribute to hypertensive disease and to problems associated with cardiac failure is supported by studies of a number of types of inhibitors of the renin-angiotensin system. Angiotensin converting-enzyme (ACE) inhibitors can slow or block the formation of angiotensin II from angiotensin I. Many drugs of this class have proved to be effective anti-hypertensive agents and are increasingly being employed in the treatment of cardiac failure. Another class of compounds, the angiotensin II receptor antagonists, are presently under clinical development. In both experimental animals and in clinical trials these compounds have shown efficacy in the treatment of hypertension. Others have sought to develop specific inhibitors of renin itself. Compounds of this class have shown efficacy in animal models and in human studies in lowering blood pressure and in treating hypertension.

Each of these classes of compounds is expected to have inhibitory action on the renin-angiotensin system wherever it may be located in the tissues of the body. The available data shows that widespread inhibition of renin or the blockade of angiotensin receptors are effective therapeutic agents. Of the three classes of agents just mentioned, only the ACE inhibitors have been in general practice long enough for the adverse effect profile to have become widely known. Among the adverse effects of these agents are rashes, disturbances of the sense of taste, vertigo, headache, hypotension, and various gastro-intestinal disturbances. Neutropenia has been described as a serious but rare toxicity. Some of these side effects have been attributed to interference with the metabolism of other bioactive molecules termed kinins; however, the evidence does not rule out interference with activity of the renin-angiotensin system in tissues other than the kidney in causing these adverse effects.

Another approach to therapeutic control of the renin-angiotensin system is to reduce the renal secretion of renin. This can be anticipated to remove the majority of circulating renin and markedly reduce angiotensin activity; yet this approach should leave local renin-angiotensin systems, in brain for example, unaffected. At least one current therapeutic approach to hypertension, $\beta$-adrenoceptor blockers such as proprandol are thought to work in part by inhibiting renal renin release (Goodman and Gillman, supra at page 195). This conclusion fits with the finding that (1) epinephrine and other $\beta$-agonists can stimulate renal renin release and (2) proprandol has been shown to reduce plasma renin levels. However, $\beta$-adrenergic agents that reduce renal renin release have significant undesirable adverse effects at effective hypotensive doses, including: cardiac depression, airways constriction, headache, lassitude, depression and gastro-intestinal disturbances. Therefore, the discovery of new agents which control renin release by novel mechanisms and lack the adverse side effects of $\beta$-blockers are desirable and important therapeutic targets.

There is also known to be a highly significant linkage between essential hypertension, hyperinsulinemia, and insulin resistance in what has been termed "Syndrome X". It was thought that the high insulin levels were an important cause of the hypertension via an action on the kidney tubules to enhance sodium retention. Newly published evidence, however, is said not to support this concept (Jarrett, R. J., "In defence of insulin: a critique of syndrome X," *The Lancet*, 340:469–471) Aug. 22, 1992)). The linkage between insulin resistance and hypertension makes the combination of anti-hypertensive activity with the ability to reduce insulin resistance, a very attractive therapy. Indeed, it has been shown that captopril, an important ACE inhibitor, has modest effects in relieving insulin resistance and this was indicated to be therapeutically advantageous. (Watson N. and Sandler M., *Curr. Med. Res. Opin.*, 12(6):374–378 (1991); Kodama J. et al., *Diabetes Care*, 13(11):1109–11111 (1990); Lithell et al., *J. Cardiovasc. Pharmacol.*, 15 Suppl. 5:S46–S52 (1990)). Thus, a therapeutic modality that acted both to reduce renin levels and to reduce insulin resistance, is a particularly attractive therapeutic target.

SUMMARY OF THE INVENTION

We have now discovered that, surprisingly in view of its previously described renal vasodilator and other properties, amylin markedly increases plasma renin activity in intact rats when given subcutaneously in a manner that avoids any disturbance of blood pressure. This is important because lowered blood pressure is a strong stimulus to renin release. We have also discovered that amylin antagonists, such as amylin receptor antagonists, including those selective for amylin receptors compared to CGRP and/or calcitonin receptors, can be used to block the amylin-evoked rise of plasma renin activity. These unexpected findings support the determination that amylin antagonists will reduce plasma renin activity with consequent therapeutic benefit in hypertension and cardiac failure and other disorders associated with elevated, inappropriate or undesired renin activity. Moreover, the additional ability of amylin antagonists to favorably modulate insulin resistance and other common metabolic disorders frequently associated with hypertension and cardiac disease provides a particularly desirable therapeutic profile.

Methods for screening for and/or evaluating antirenin amylin antagonists are also described.

DETAILED DESCRIPTION OF THE INVENTION

Figure 1A:
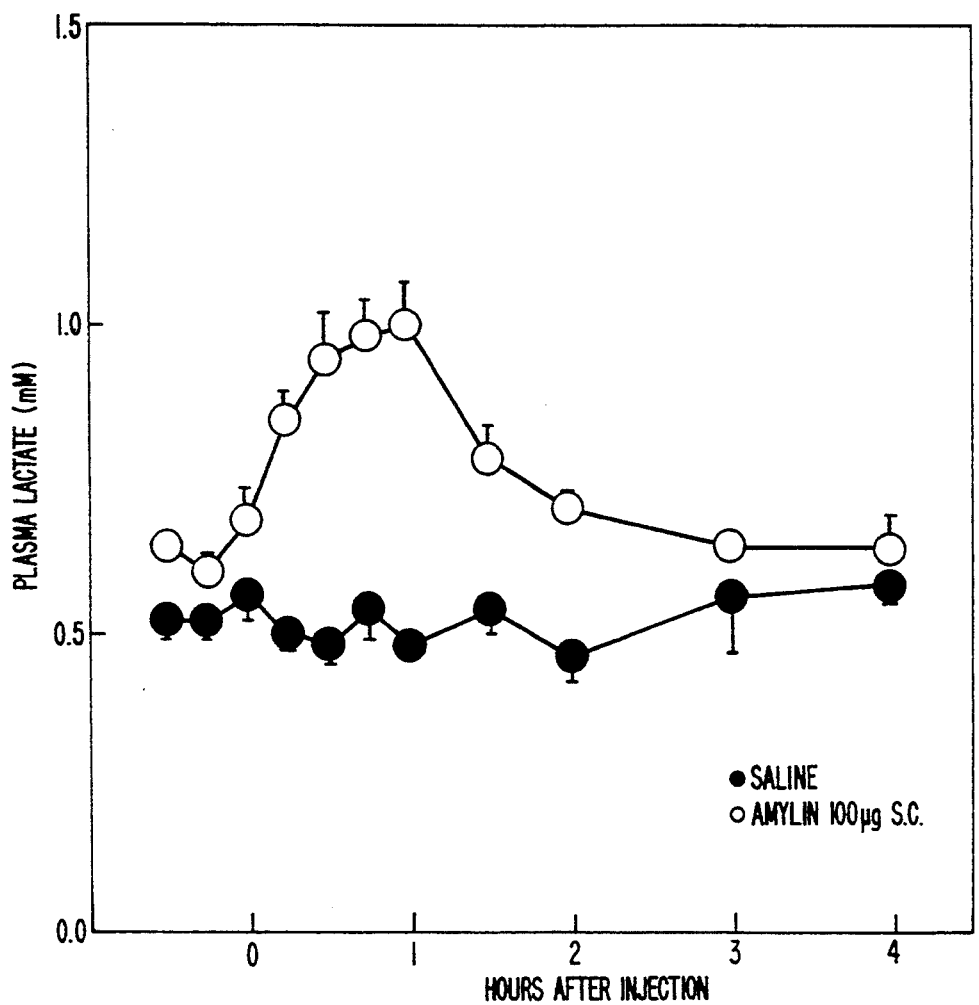
FIG. 1a shows the change in plasma lactate following subcutaneous injection of 100 μg of rat amylin or equivalent volume of saline vehicle into experimental animals.

The method of the present invention can employ any amylin antagonists, including amylin receptor antagonists such as $^{8-37}$CGRP, $^{8-37}$amylin or $^{8-32}$calcitonin. Examples of other suitable amylin receptor antagonists include $^{8-37}$CGRP(human), $^{8-37}$amylin(rat), $^{8-32}$calcitonin(salmon), and $^{8-32}$calcitonin(eel). Other useful amylin receptor antagonist compounds are acetyl-$^{30}$Asn$^{32}$Tyr$^{8-32}$calcitonin(salmon) and acetyl-$^{11,18}$Arg-$^{30}$Asn$^{32}$Tyr-$^{9-32}$calcitonin(salmon); $^{14}$Asp$^{15}$Phe$^{23}$Gly$^{8-37}$CGRP; $^{9-37}$CGRP; $^{11-37}$CGRP; $^{18-37}$CGRP; $^{26}$Asp$^2$-$^7$Val$^{29}$Ala$^{8-32}$calcitonin(salmon); $^{30}$Asn$^{32}$Tyr$^{8-32}$calcitonin(salmon); acetyl-$^{9-32}$calcitonin(salmon); acetyl-$^{30}$Asn$^{32}$Tyr$^{9-32}$calcitonin(salmon); $^{9-23}$calcitonin(salmon)-$^{29-37}$amylin; acetyl-$^{9-23}$calcitonin(salmon)$^{29-37}$amylin; adamantyl-$^{9-23}$calcitonin(salmon)$^{29-37}$amylin; acetyl-$^{11}$Arg$^{15}$Leu$^{18}$Arg$^{30}$Asn$^{32}$Tyr$^{9-32}$calcitonin(salmon); acetyl-$^{11}$Arg$^{18}$Arg$^{30}$Asn$^{32}$Tyr$^{9-32}$calcitonin(salmon); acetyl-$^{18}$Arg$^{30}$Asn$^{32}$Tyr$^{9-32}$calcitonin(salmon). Still further amylin antagonists are disclosed in U.S. patent application Ser. No. 794,288, filed on Nov. 19, 1991, the disclosure of which is hereby incorporated by reference. The activity of these amylin antagonists may be evaluated using certain biological assays described herein. The receptor binding assay can identify both candidate amylin agonists and antagonists and can be used to evaluate binding, while the soleus muscle assay distinguishes between amylin agonists and antagonists. Effects of amylin antagonists on kidney tissue and, specifically, renin activity, can be evaluated using the methods described in the Example below.

Preferably, these antagonist compounds exhibit activity in the receptor binding assay on the order of less than about 1 to 5 nM, preferably less than about 1 nM and more preferably less than about 50 pM. In the soleus muscle assay these compounds preferably show IC$_{50}$ values on the order of less than about 1 to 2 micromolar.

The receptor binding assay is described in U.S. patent application Ser. No. 670,231, filed on Mar. 15, 1991, the disclosure of which is incorporated herein by reference. The receptor binding assay is a competition assay which measures the ability of compounds to bind specifically to membrane-bound amylin receptors. A preferred source of the membrane preparations used in the assay is the basal forebrain which comprises membranes from the nucleus accumbens and surrounding regions. Compounds being assayed compete for binding to these receptor preparations with $^{125}$I Bolton Hunter rat amylin. Competition curves, wherein the amount bound (B) is plotted as a function of the log of the concentration of ligand are analyzed by computer, using analyses by nonlinear regression to a 4-parameter logistic equation (Inplot program; GraphPAD Software, San Diego, Calif.) or the ALLFIT program of DeLean et. al. (ALLFIT, Version 2.7 (NIH, Bethesda, Md. 20892)). Munsun, P. U. and Rodbard, D., *Anal. Biochem.* 107:220–239 (1980).

Assays of biological activity of amylin preparations in the soleus muscle are performed using previously described methods (Leighton, B. and Cooper, G. J. S., *Nature*, 335:632–635 (1988); Cooper, G. J. S., et al. *Proc. Natl. Acad. Sci. USA* 85:7763–7766 (1988)). In summary, amylin agonist activity is assessed by measuring the inhibition of insulin-stimulated glycogen synthesis in soleus muscle. Amylin antagonist activity is assessed by measuring the resumption of insulin-stimulated glycogen synthesis in the presence of 100 nM rat amylin and an amylin antagonist. Concentrations of peptide dissolved in carrier-free buffers are determined by quantitative amino acid analysis, as described therein. The ability of compounds to act as antagonists in this assay is determined by measuring IC$_{50}$ values. Standard errors are determined by fitting of sigmoidal dose response curves using a four parameter logistic equation (De Lean, A., Munson, P. J., Guardabasso, V. and Rodbard, D. (1988) ALLFIT, Version 2.7, National Institute of Child Health and Human Development, N.I.H. Bethesda, Md., 1 diskette). A number of amylin antagonists have been characterized using these biological assays. The compounds $^{8-37}$amylin, $^{8-37}$CGRP and $^{8-32}$calcitonin(salmon) were all found to compete with amylin in the receptor binding assay. These compounds have negligible agonist activity as measured by the soleus muscle assay and were shown to act as amylin antagonists. Similar results were obtained with the other antagonist compounds listed above.

Compounds such as those described above are prepared using standard solid-phase peptide synthesis techniques and preferably an automated or semiautomated peptide synthesizer. Typically, an α-N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The α-N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer were purchased from Applied Biosystems Inc. (Foster City, Calif.), unless otherwise indicated. The side-chain protected amino acids used. and purchased from Applied Biosystem, Inc. included the following: Boc-Arg(Mts), Fmoc-Arg(Pmc), Boc-Thr(Bzl), Fmoc-Thr(t-Bu), Boc-Ser(Bzl), Fmoc-Ser(t-Bu), Boc-Tyr(BrZ), Fmoc-Tyr(t-Bu), Boc-Lys(Cl-Z), Fmoc-Lys(Boc), Boc-Glu(Bzl), Fmoc-Glu(t-Bu), Fmoc-His(Trt), Fmoc-Asn(Trt), and Fmoc-Gln(Trt). Boc-His(BOM) was purchased from Applied Biosystems, Inc. or Bachem Inc. (Torrance, Calif.). Anisole, methylsulfide, phenol, ethanedithiol, and thioanisole were obtained from Aldrich Chemical Company (Milwaukee, Wis.). Air Products and Chemicals (Allentown, Pa.) supplied HF. Ethyl ether, acetic acid and methanol were purchased from Fisher Scientific (Pittsburgh, Pa.).

Solid phase peptide synthesis was carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49-70, Applied Biosystems, Inc., Foster City, Calif.) with capping. Boc-peptide-resins were cleaved with HF ($-5°$ C. to $0°$ C., 1 hour). The peptide was extracted from the resin with alternating water and acetic acid, and the filtrates were lyophilized. The Fmoc-peptide resins were cleaved according to standard methods (*Introduction to Cleavage Techniques*, Applied Biosystems, Inc., 1990, pp. 6-12 ). Some peptides were also assembled using an Advanced Chem Tech Synthesizer (Model MPS 350, Louisville, Ky.). Peptides were purified by RP-HPLC (preparative and analytical) using a Waters Delta Prep 3000 system. A C4, C8 or C18 preparative column (10μ, 2.2×25 cm; Vydac, Hesperia, Calif.) was used to isolate peptides, and purity was determined using a C4, C8 or C18 analytical column (5μ, 0.46×25 cm; Vydac). Solvents (A=0.1% TFA/water and B=0.1% TFA/CH$_3$CN) were delivered to the analytical column at a flowrate of 1.0 ml/min and to the preparative column at 15 ml/min. Amino acid analyses were performed on the Waters Pico Tag system and processed using the Maxima program. The peptides were hydrolyzed by vapor-phase acid hydrolysis ($115°$ C., 20-24 h). Hydrolysates were derivatized and analyzed by standard methods (Cohen, S. A., Meys, M., and Tarrin, T. L. (1989), *The Pico Tag Method: A Manual of Advanced Techniques for Amino Acid Analysis*, pp. 11-52, Millipore Corporation, Milford, Mass.). Fast atom bombardment analysis was carried out by M-Scan, Incorporated (West Chester, Pa.). Mass calibration was performed using cesium iodide or cesium iodide/glycerol. Plasma desorption ionization analysis using time of flight detection was carried out on an Applied Biosystems Bio-Ion 20 mass spectrometer.

Peptide compounds useful in the invention may also be prepared using recombinant DNA techniques, using methods now known in the art. See, e.g., Sambrook et al., *Molecular Cloning: A Laboratory Manual*, 2d Ed., Cold Spring Harbor (1989).

The compounds referenced above form salts with various inorganic and organic acids and bases. Such salts include salts prepared with organic and inorganic acids, for example, HCl, HBr, H$_2$SO$_4$, H$_3$PO$_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The compounds described above are useful in view of their pharmacological properties. In particular, the compounds of the invention possess activity as anti-amylin and anti-renin agents, as evidenced by the ability to reduce renin in mammals. compositions or products of the invention may conveniently be provided in the form of formulations suitable for parenteral (including intravenous, intramuscular and subcutaneous) or nasal or oral administration. In some cases, it will be convenient to provide an amylin antagonist of the invention and another anti-hypertensive agent, such as an ACE inhibitor, in a single composition or solution for administration together. In other cases, it may be more advantageous to administer an ACE inhibitor or other anti-hypertensive agent (such as a diuretic, a cardiotonic agent, or a beta-adrenergic blocker) separately from said amylin inhibitor. A suitable administration format may best be determined by a medical practitioner for each patient individually. Suitable pharmaceutically acceptable carriers and their formulation are described in standard formulation treatises, e.g., *Remington's Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988). Suitable formulations including hypoglycemic agents such as sulfonylureas are known in the art.

The products of the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include sodium citrate-citric acid and sodium phosphate-phosphoric acid. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

The therapeutically useful compositions of the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of an antagonist compound of the invention with or without another anti-hypertensive agent which will be effective in one or multiple doses to control or reestablish blood sugar at the selected level. Therapeutically effective amounts of an amylin antagonist as described herein for the treatment or prevention of elevated renin and other such conditions in which renin activity is beneficially reduced are those that decrease blood renin activity, preferably to no more than about fifty percent of pretreatment levels or such that blood pressure levels are reduced as desired. In some hypertensive individuals, plasma renin activity is not higher than in normotensive individuals. It can nonetheless be regarded as inappropriate and, in such individuals, beneficial reduction of arterial pressure, for example, may be obtained without changes in plasma renin activity (see Wilson, J. D. and Foster, D. W., *Williams Text Book of Endocrinology*, page 714 (8th Edition 1992)). Therapeutically effective amounts of an amylin antagonist for the treatment of insulin resistance are those that increase the effectiveness of insulin, preferably by about 20%, as may be determined using methods described herein and known in the art. Therapeutically effective amounts of an amylin antagonist for the treatment of cardiac failure are those that reduce amylin action by about 25% or that produce beneficial therapeutic effect as determined by the physician for the individual patient. As will be recognized by those in the field, an effective amount of therapeutic agent will vary with many factors including the age and weight of the patient, the patient's physical condition, the blood sugar level or decrease in amylin action to the obtained, and other factors.

Such pharmaceutical compositions are useful in the treatment of hypertension, cardiac failure (including congestive cardiac failure), as well as other disorders where renin action is beneficially reduced.

The effective daily anti-renin dose of the compounds of this invention will typically be in the range of 0.05 to about 1000 mg/day, preferably about 1 to 500 mg/day for a 70 kg patient, administered in a single or divided doses. The exact dose to be administered is determined by the attending clinician and is dependent upon where the particular compound lies within the above quoted range, as well as upon the age, weight and condition of the individual. Administration should begin at the first sign of symptoms or shortly after diagnosis of diabetes mellitus.

Generally, in treating or preventing elevated, inappropriate, or undesired renin activity, the compounds of this invention may be administered to patients in need of such treatment in a dosage range of about 0.1 mg to 50 mg per patient generally given one, two, or three times a day, thus giving a total dose of from about 0.3 mg to 200 mg per day.

To assist in understanding the present invention, the following Example is included which describes the results of a series of experiments. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE

Male Harlan Sprague Dawley rats were housed at 22.7°±0.8° C. in a 12:12 hour light:dark cycle (experiments being performed during the light cycle) and fed and watered ad libitum (Diet LM-485, Teklad, Madison, Wis.). Animals used were aged 87–94 days and weighed 353–392 g. They were deprived of food for ~20 hours prior to experimentation.

Anesthesia was induced with 5% halothane, maintained at 2% during surgery and at 0.8–1% during recordings. Tracheotomy and cannulation of the right femoral artery and saphenous vein were performed. The femoral arterial line was connected to a pressure transducer (Spectramed P23XL transducer, Model 13-4615-58 amplifier, Gould, Cleveland, Ohio) and perfused with heparinized saline (2 U/ml) at 3.0 ml/hr. Colonic temperature was measured using a thermistor probe and controller (Model 73A, YSI, Yellow Springs, Ohio) which provided closed-loop control of core temperature by switching a heated operating table. The signal for mean arterial pressure was periodically sampled and stored with 12-bit precision at 1 Hz using a computerized data acquisition system (DT2801A A/D converters, DataTranslation, Marlboro, Mass.; AST Premium 386 computer, AST Research, Irvine, Calif.; Labtech Notebook software, Laboratory Technologies Corp, Wilmington, Mass.).

Synthetic rat amylin (Bachem, Torrance, Calif.) was tested for its ability to bind in the amylin receptor assay, and for bioactivity using the soleus muscle-based assay. The amylin antagonist acetyl-$^{30}$Asn$^{32}$Tyr$^{8-32}$calcitonin(salmon) was made by solid phase peptide synthesis as described above.

The following treatment groups were utilized: (1) control rats (n=5) which, at t=0, were injected subcutaneously with 0.1 mL of 0.15M saline; (2) amylin injection rats (n=5) which, at t=0, were administered 100 μg synthetic rat amylin in 0.1 mL saline as a subcutaneous bolus into the ventral abdominal wall; and (3) amylin injection following antagonists preinfusion rats (n=1). In group 3, subcutaneous amylin injection (as in Group 2) was preceeded by a primed/continuous intravenous infusion of the specific amylin antagonist, acetyl-$^{30}$Asn$^{32}$Pyr$^{8-32}$calcitonin(salmon). A bolus intravenous dose of 0.5 mg of antagonist at −30 min was followed by a 1 mg/hr intravenous infusion until t=120 min.

Arterial samples of 250 μL were drawn into nonheparinized Natelson tubes at −30, −15, 0, 15, 30, 45, 60, 90 and 120 minutes (relative to amylin injection), transferred to chilled EDTA microfuge tubes, spun, and the separated plasma analyzed immediately for glucose and lactate using immobilized enzyme chemistries (glucose oxidase, L-lactate oxidase, Analyzer model 2300-STAT, YSI, Yellow Springs, Ohio). The remainder was frozen at −20° C. for measurement of plasma renin activity. Plasma renin activity was measured using the Gammacoat TM [$^{125}$I] radioimmunoassay kit (Incstar Corp, Stillwater, Minn.) modified to accomodate small sample volumes. The assay system measured the renin-catalysed rate of generation of angiotensin-I in the presence of phenylmethylsulfonyl fluoride (PMSF) to prevent its proteolytic breakdown and/or conversion to angiotensin-II. Angiotensin-I generated in 90 minutes at 37° C. was then detected by specific radioimmunoassay with less than 0.02% cross reactivity to angiotensin-II, angiotensin-III or tetradecapeptide (renin substrate). The intra-run coefficient of variation was 4.6–10% and the inter-run (means of duplicates) was 5.6–6.8% Renin levels were expressed as units of activity (ng of Angiotensin-I generated per hour) per mL of plasma.

Figure 1B:
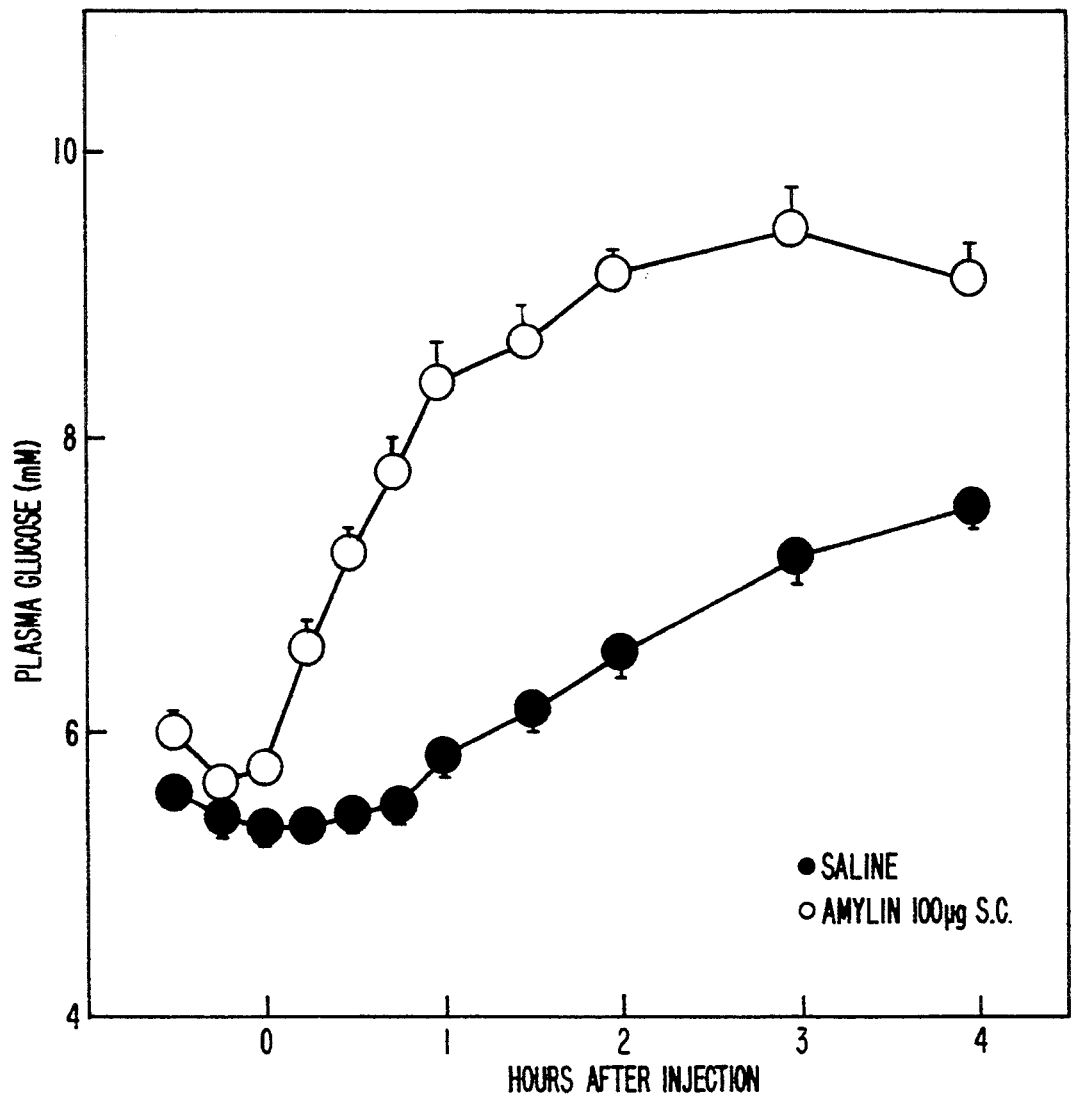
FIG. 1b shows the change in plasma glucose following subcutaneous injection of 100 μg of rat amylin or equivalent volume of saline vehicle into experimental animals.
Figure 1C:
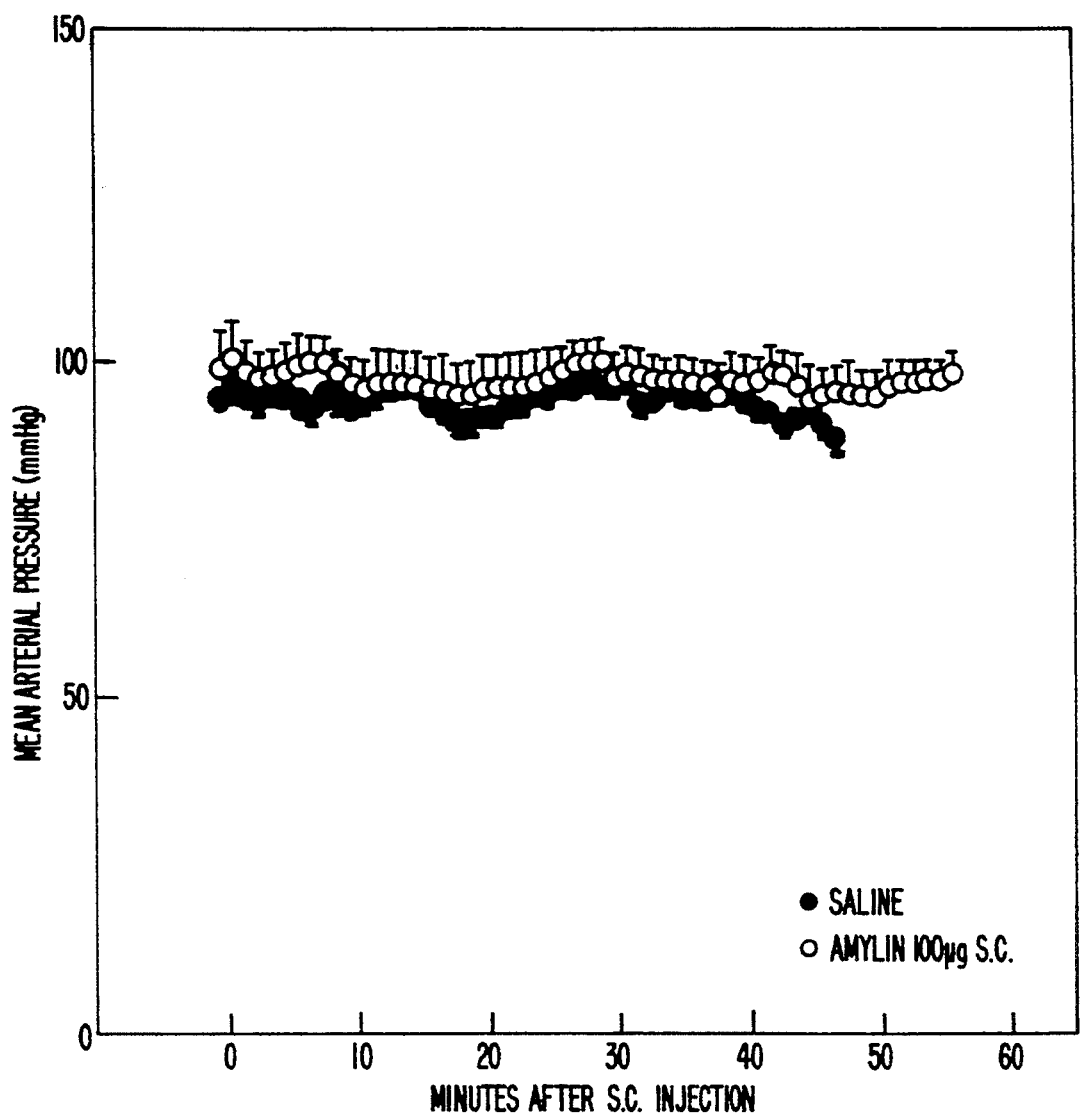
FIG. 1c shows the lack of change in mean arterial pressure upon administration of 100 μg of rat amylin or equivalent volume of saline vehicle into experimental animals.
Figure 1D:
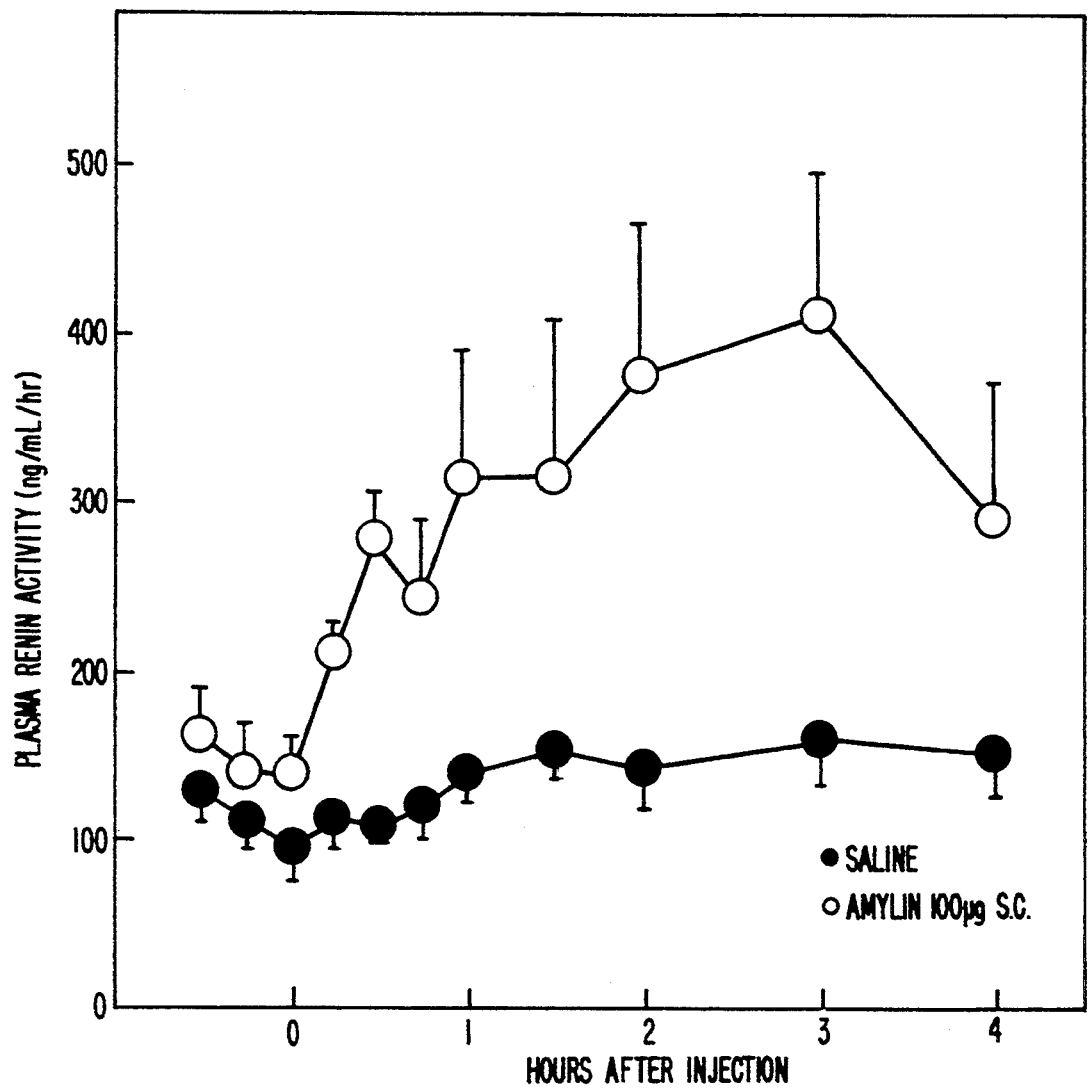
FIG. 1d shows the change in plasma renin activity in experimental animals administered rat amylin as compared to control.

FIGS. 1a and 1b show the change in plasma lactate and plasma glucose following the subcutaneous injection of 100 μg of rat amylin or the eqivalent volume of saline vehicle. These changes are similar to those previously reported with this dose and route of administration. FIG. 1c shows that this dose and route of administration was not associated with any significant change in mean arterial pressure in either amylin or saline injected rats. This observation, also consistent with previous reports, contrasts to the decreases in mean arterial pressure observed when 100 μg of amylin is injected intavenously into rats. FIG. 1d indicates a 3- to 4-fold elevation of plasma renin activity in rats administered s.c. amylin compared to saline-treated controls. The principal causes of renin release recognized before now have been (1) low plasma sodium, (2 ) renal hypotension, and (3) β-adrenergic stimulation. Comparison of FIGS. 1c and 1d show that the elevation of plasma renin activity following s.c. amylin was unassociated with any change in mean arterial pressure and is therefore unlikely to be associated with or a consequence of renal hypotension.

Figure 2:
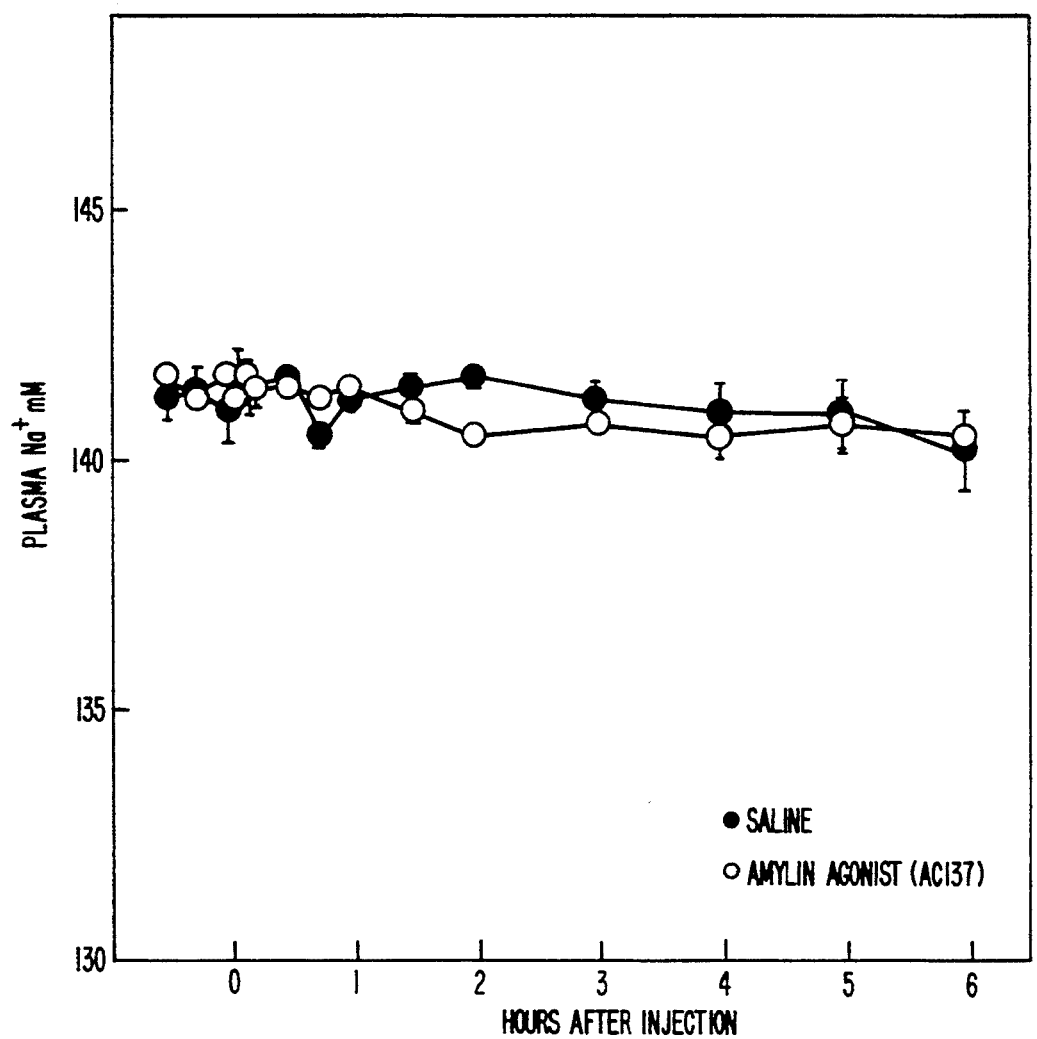
FIG. 2 shows the lack of an acute change in plasma sodium in experimental animals following administration of AC-137, an amylin agonist compound.

The data in FIG. 2 were obtained following the intravenous injection of an amylin agonist (AC137), and show that amylin action is unassociated with any acute change in plasma sodium. It has previously been reported that amylin administration is not associated with an increase in plasma catecholamines. Amylin thus acts by mechanisms not previously identified to stimulate renin release.

Figure 3:
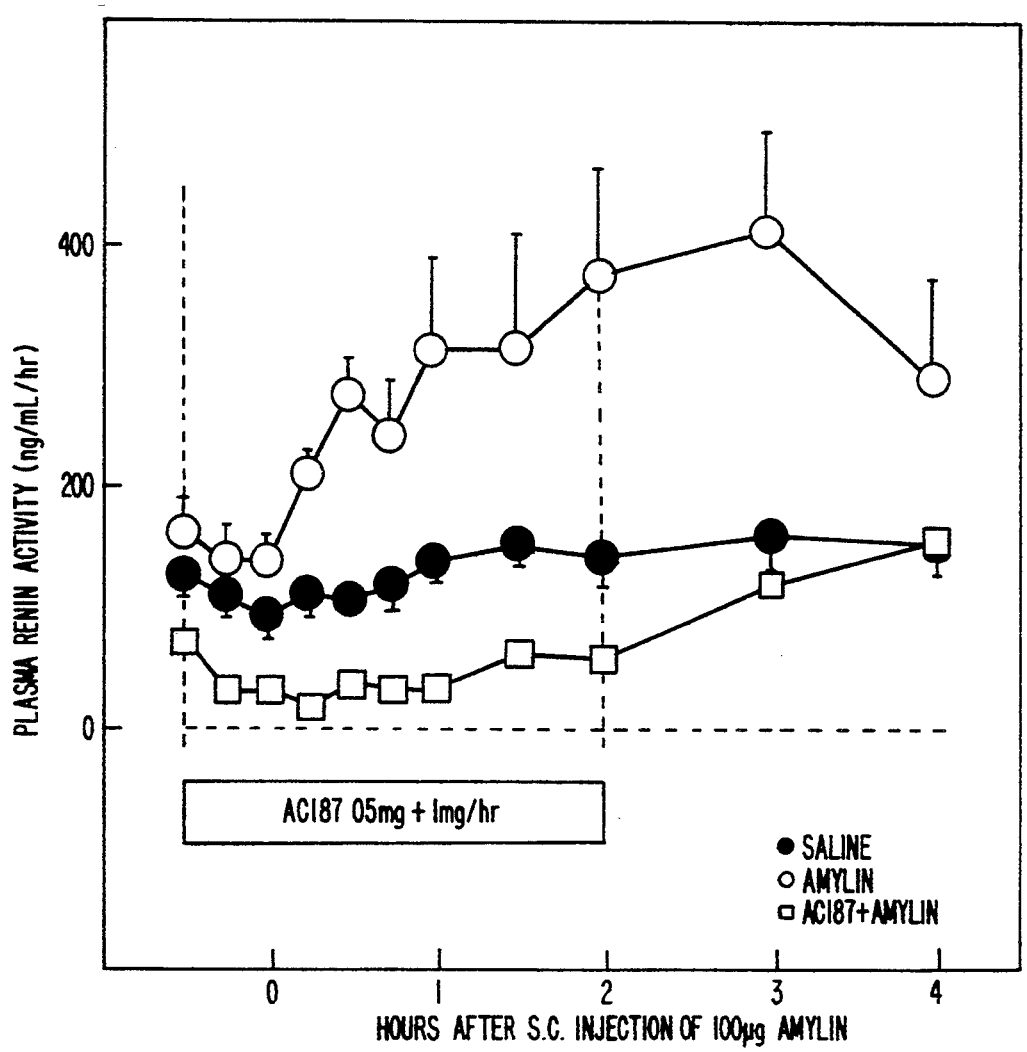
FIG. 3 shows the plasma renin activity in an experimental animal preinfused with an amylin antagonist prior to subcutaneous injection of rat amylin.

FIG. 3 shows the plasma renin activity in a rat preinfused with the amylin antagonist acetyl-$^{30}$Asn$^{32}$Tyr-$^{8-32}$calcitonin(salmon) (Group 3) prior to subcutaneous injection of rat amylin. There is no amylin-induced elevation of plasma renin activity. The amylin antagonist infusion also prevented the amylin-induced increase in plasma lactate and glucose.

Figure 4:
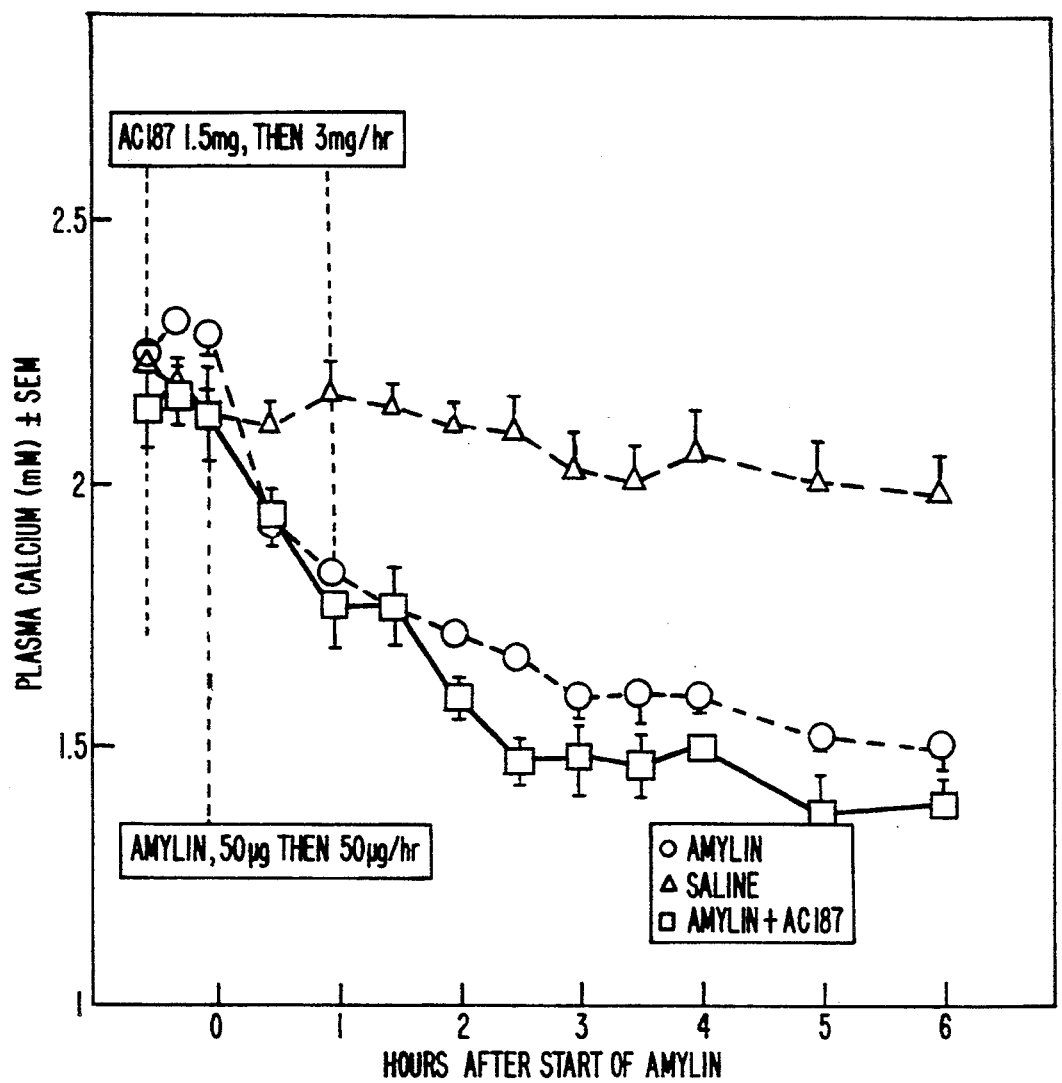
FIG. 4 shows the lack of change in amylin-induced hypocalcemia in experimental animals preinfused with an amylin antagonist prior to subcutaneous injection of rat amylin.

It was separately shown that the antagonist is selective for amylin receptors over calcitonin and CGRP receptors. Infusion of acetyl-$^{30}$Asn$^{32}$Tyr$^{8-32}$calcitonin(salmon) at three times the rate used in the above-described experiments (1.5 mg+3 mg/hr) did not prevent amylin-induced hypocalcemia (see FIG. 4). Thus, if amylin-induced hypocalcemia is due to action at calcitonin receptors, then at these doses the amylin antagonist acetyl-$^{30}$Asn$^{32}$Tyr$^{8-32}$calcitonin(salmon) does not block these calcitonin receptors. This supports the conclusion amylin antagonist blockade of amylin-induced renin release is mediated by blockade of receptors other than calcitonin receptors. Similarly, the amylin antagonist acetyl-$^{30}$Asn$^{32}$Tyr-$^{8-32}$calcitonin(salmon) has low affinity for CGRP receptors in vitro and at three times the dose used in this study, it does not fully block the hypotensive response to intravenous amylin in vivo (attributed to vascular CGRP$_1$ receptor stimulation). Its effective blockade of renin release indicates that amylin-stimulated renin release is mediated via amylin receptors and amylin antagonists can be expected to reduce renin release in the presence of biologically effective amounts of amylin.

We claim:

1. A method for ameliorating renin activity in a subject which comprises administering to said subject an effective amount of an amylin antagonist.

2. The method of claim 1 wherein said amylin antagonist is an amylin receptor antagonist.

3. The method of claim 2 wherein said amylin receptor antagonist is selective for amylin receptors relative to calcitonin or CGRP receptors.

4. A method for treating or preventing the development of cardiac failure in a subject which comprises administering to said subject an amount of an amylin antagonist effective to reduce renin activity in said subject.

5. The method of claim 4 wherein said cardiac failure is congestive cardiac failure.

6. A method for treating syndrome X in a subject which comprises administering to said subject an effective amount of an amylin antagonist.

7. A method for treating a subject suffering from hypertension and hyperamylinemia which comprises administering to said subject an effective amount of an amylin antagonist.

8. A method of treating a subject suffering from hypertension and hyperinsulinemia which comprises administering to said subject an effective amount of an amylin antagonist.

9. A method of treating a hypertensive, insulin-resistant subject suffering from coronary artery disease and having hyperamylinemia or hyperinsulinemia which comprises administering to said subject an effective amount of an amylin antagonist.

* * * * *